United States Patent
Cho

Patent Number: 5,921,246
Date of Patent: Jul. 13, 1999

[54] METHOD FOR SURGICALLY ENLARGING A PENIS

[76] Inventor: Kang-Seon Cho, Samseong-dong, Kangnam-gu, Seoul, Rep. of Korea

[21] Appl. No.: 09/111,643

[22] Filed: Jul. 8, 1998

[30]     Foreign Application Priority Data

Jan. 19, 1998  [KR]  Rep. of Korea ...................... P98-1452

[51] Int. Cl.⁶ ..................................................... A61B 19/00
[52] U.S. Cl. ............................................................ 128/898
[58] Field of Search .............................. 128/898; 623/11, 623/12, 66, 7; 600/36, 40

[56]     References Cited

FOREIGN PATENT DOCUMENTS 408257045  10/1996  Japan ........................................ 623/66

*Primary Examiner*—Mickey Yu
*Assistant Examiner*—K. O'Hara
*Attorney, Agent, or Firm*—Merchant, Gould, Smith, Edell, Welter & Schmidt

[57]     ABSTRACT

A surgically enlarging method of microcaulia by which length and circumference of micropenis are simultaneously enlarged and expanded without incurring any deformation or side effect thereto, enabling the microcaulia patients to overcome the physical defect, shame and inferiority complex and thereby providing them with increased sexual self confidence.

2 Claims, 4 Drawing Sheets

METHOD FOR SURGICALLY ENLARGING A PENIS

BACKGROUND OF THE INVENTION

1. Field of the Invention

The present invention relates to a surgically enlarging method of microcaulia adapted to enlarge or elongate length and circumference of a penis in an unerectile state, without giving rise to deformation or side effect thereto alleviating a shame of a microcaulia neurotic, eliminating an inferiority complex, and thereby providing an emotional stability for maintenance of a normal life.

2. Description of the Prior Art

Generally, microcaulia neurosis denotes a variety of neurotic symptoms resulting from a feeling that his penis is smaller than those of other men.

There are cases of underdeveloped micropenis, however self-consciousness of his male being smaller dominates most of the cases even though his penis has normally developed objectively.

There is no standardized definition of accurately defining the microcaulia, however, a penis is regarded as small when it is measured less than 4 cm from an upper pubis to a tip end thereof in the absence of erection state or when the standard deviation is more than 2 compared with a normal penile length of the same age group.

The microcaulia occurs when the penis is underdeveloped due to deficiencies of testosterone. This should not be treated as an independent physical disorder but regarded as a general disorder affecting whole target tissue against androgen.

In this case, testicles are generally small or the micropenis is accompanied by retained testicles. At times, underdeveloped scrotum happens, and chances are that patients of micropenes suffer from prostate problems and incomplete physical growth at post-pubescence.

Microcaulia neurotics (patients) usually have inferiority complexes and lacks self-confidence in everyday lives, and especially they hate to go out to people-gathering places in nudity such as public bath houses and the like, thereby experiencing lots of inconveniences in social lives.

As mentioned above, in order to treat the microcaulia neurotics, it is necessary to both enlarge and expand the length and girth of a penis and at the same time to maintain a natural look thereof.

Currently, surgical treatment include a girth enlargement surgery of penis by way of derma fat transplant, a length elongation surgery of penis by way of ligament cut and expansion of skin length and the like. These kinds of surgeries are done separately.

In more detail, the former method of girth enlargement surgery is performed by tearing off derma fat from part of the body, incising the skin of penis at a predetermined width and grafting the torn derma fat to the girth of the penis except for urethra area, to thereby expand the circumference of the penis.

The latter method of length elongation surgery is carried out by incising a suspensor ligament of the penis, expanding the skin length and enlarging the overall length of penis, whereby, in case of success in surgery, the penis is in most cases enlarged lengthwise by as short as 2.5 cm in an unerectile state to the dismay of patient.

SUMMARY OF THE INVENTION

However, there is a problem in the girth enlargement surgery in that only the girth is expanded and extra surgery should be performed to get an effective treatment of length elongation. There is also a problem in the length elongation surgery in that success rate is low, and even in case of success, the elongated length is not that long (generally less than 2.5 cm) and the odds after the surgery are the length of the penis is rather shortened during erection or the penis tends to droop down.

There is still another problem in the length elongation surgery in that shape of penis is unnaturally deformed, thereby providing a cause of another complex feeling so that these kinds of surgical methods cannot be ragarded as appropriate cures to the microcaulia neurotics.

Accordingly, the present invention is presented to solve the afore-mentioned problems and it is an object of the present invention to provide a surgically enlarging method of microcaulia adapted to simultaneously enlarge and lengthen the girth and the length of a micropenis with no side effect incurred and increased surgical success rate (99.8%) and at the same time to maintain a natural look thereof.

In accordance with the objects of the present invention there is provided a surgically enlarging method of microcaulia, the method comprising the steps of:

tearing off a piece of derma fat from the body of a microcaulia neurotic to put the torn derma fat in cold storage and suturing the vulnus area for cosmetic surgery;

incising the skin of penis and ablating same to graft the cold-stored derma fat onto the ablated area of penis in a state of the penis being maximally pulled to a front area thereof to similarly match the length of the penis; and covering the implanted derma fat with the ablated skin of penis to suture the covered area and to fix same.

BRIEF DESCRIPTION OF THE DRAWINGS

For fuller understanding of the nature and objects of the invention, reference should be made to the following detailed description taken in conjunction with the accompanying drawings in which.

DETAILED DESCRIPTION OF THE INVENTION

A preferred embodiment of the present invention will now be described in detail with reference to the accompanying drawings.

Figure 1:
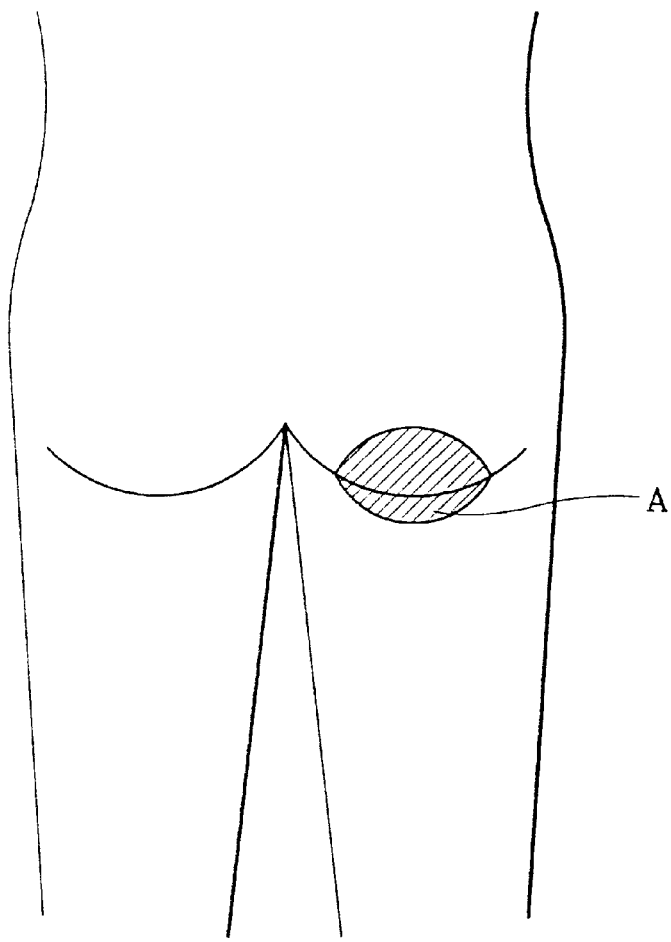
FIG. 1 is a schematic diagram for illustrating a tearing-off of derma fat from a wrinkled hip area of a patient.

First of all, the microcaulia neurotic is layed down on belly to tear out as much derma fat (A) as possible from part of the body, preferably from a wrinkled hip area as illustrated in FIG. 1, the derma fat (A) being large enough to cover the penis circumferentially.

The derma fat is put to cold storage in a lower temperature, preferably 0° C., right after it is torn out. The vulnus (torn) area where the derma fat is taken out is sutured by cosmetic surgery.

At this time, the torn derma fat should be long and wide enough to circumfuse an erect penis lest there should be any problem in suturing the vulnus area. The reason of putting the torn derma fat (A) in a cold storage is to minimize damages of cells in the derma fat (A) before the graft is performed (approximately 60 minutes).

The patient is then made to lie down after the suture and cosmetic surgery are carried out, and the patient's penis is cut by a surgical scalpel (See FIG. 3) and the skin of the penis is fully ablated from a cut line (B) to the direction of glans and upper part of pubis ("C" direction) to expose Buck's Fascia (Buck's muscle membrane). (See FIG. 4)

Figure 4:
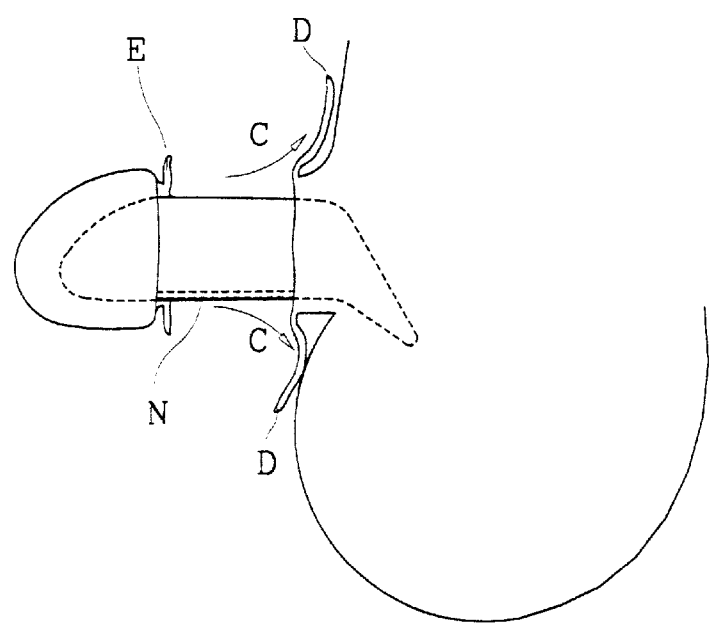
FIG. 4 is a schematic diagram for illustrating ablations of skin of the penis from respective incision lines.

Reference symbol "D" in FIG. 4 is the skin of penis ablated from the upper part of pubis ("C" direction) and "E" is another skin of penis separated from the glans.

Figure 5:
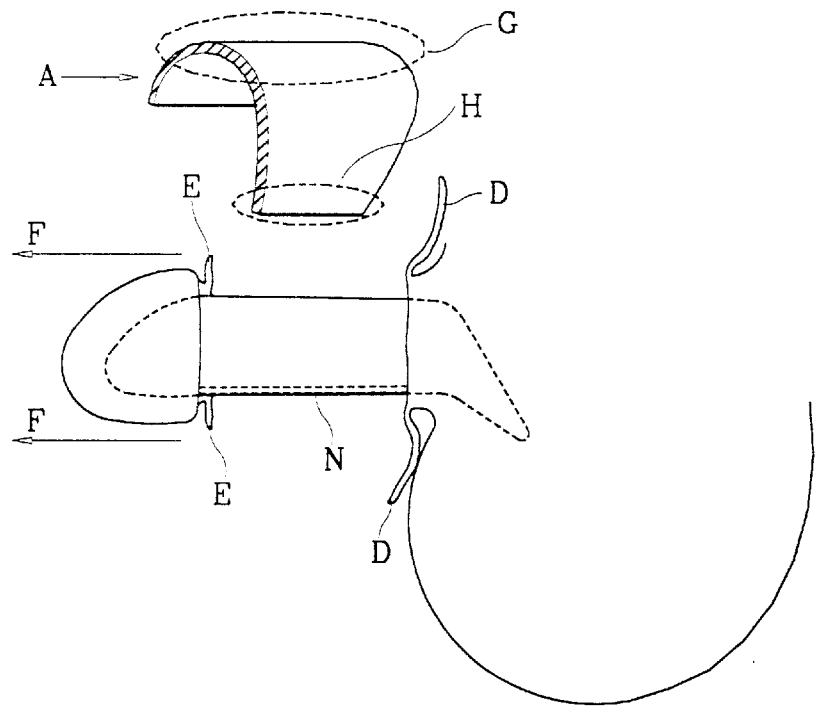
FIG. 5 is a schematic diagram for illustrating an implantation of derma fat torn from the ablated penis area in a state of the penis maximally pulled to the front thereof.

Next, as illustrated in FIG. 5, the penis of the patient is maximally pulled forward ("F" direction) to almost the same length of erection under which state the cold-stored derma fat (A) is grafted to the ablated area of the penis.

Figure 2:
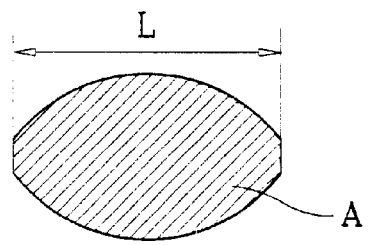
FIG. 2 is a schematic diagram for illustrating a derma fat cut at both sides, leaving the length (L) of the derma fat to fully cover the circumference of a penis.

At this time, the torn derma fat (A) is cut at both end sides except for the portion which can fully encompass the penis, as illustrated in FIG. 2.

Successively, derma layer is made to face outside of the penis in a bit unfolded state, that is, in a non-stretched state of the derma fat (A) and fat layer is made to face the penis.

Meanwhile, the widest area (G) of the torn derma fat (A) is positioned at an upper side (12 o'clock direction) of the penis and the narrowest area (H) is made to be situated under the penis (6 o'clock direction).

At this location, the torn derma fat (A) is made to be positioned in such a way as to encompass the whole length of the penis including the urethra part (N) such that the torn derma fat (A) should have enough room not to interfere circumferential expansion of the penis when it is erected. The derma fat (A) is then sutured and fixed to Buck's Fascia.

Figure 6:
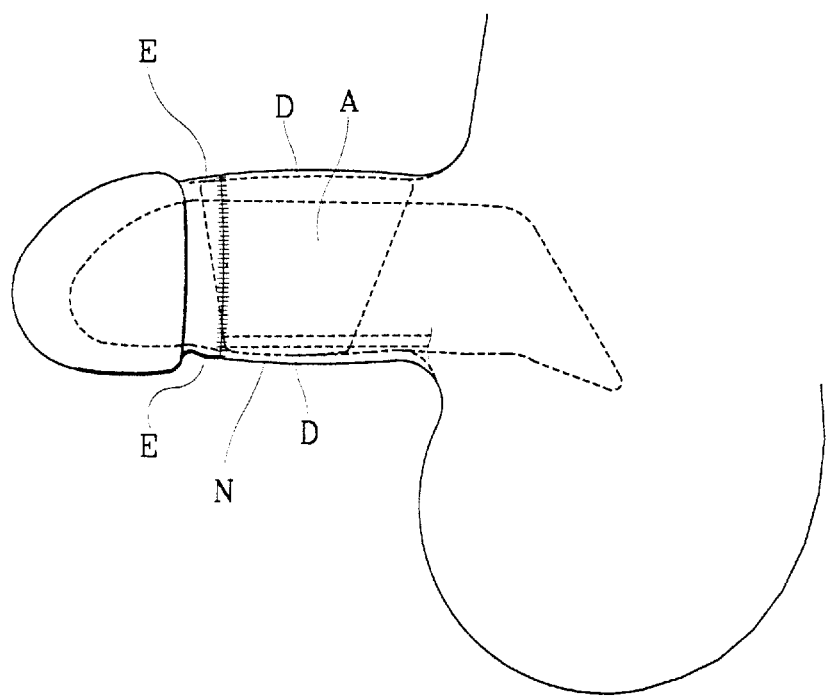
FIG. 6 is a schematic diagram for illustrating a sutured state of the ablated skin of penis onto the derma fat after the derma fat is implanted.

The dorma fat (A) grafted to the penis is sequentially covered with and sutured by subcutaneous tissue and skin tissue of the penis respectively ablated towards the glans and the upper part of pubis ("C" direction), as illustrated in FIG. 6.

Figure 7:
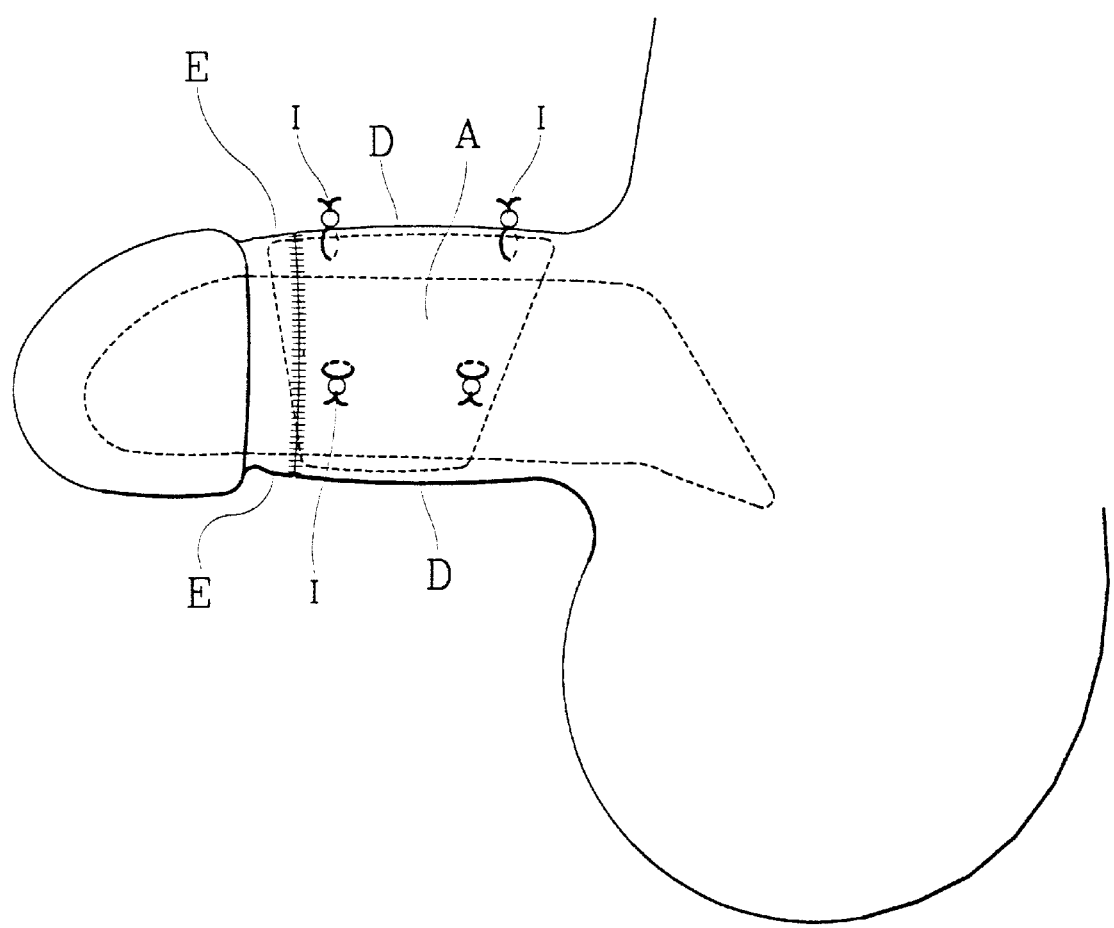
FIG. 7 is a schematic diagram for illustrating a sutured state where an original skin tissue and grafted derma fat tissue are all sewn at an external side of the penis in order to mutually fix the original skin tissue and the derma fat tissue grafted on the penis and petrolatum gauze is applied to the external side of the penis skin on which a knot is tied for suture.

At next stage, as illustrated in FIG. 7, the original skin tissue and the grafted derma fat tissue are all sewn together at an external side of the penis so as to be fixed therebetween. The external side of the penis is then applied by petrolatum gauze (I) on which a knot is made and sutured.

Figure 3:
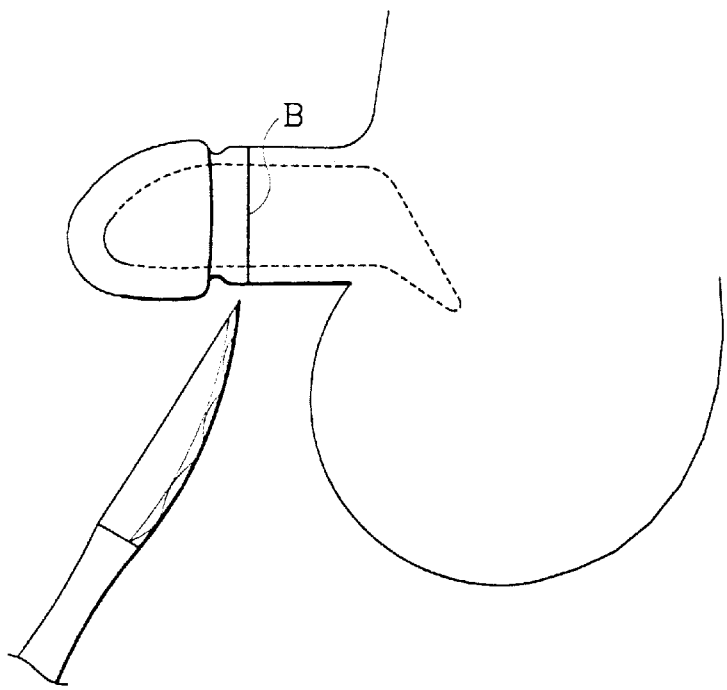
FIG. 3 is a schematic diagram for illustrating an incision of a penis.

Accordingly, as comparatively seen in FIG. 3 and FIG. 6, the hip derma fat tissue (A) implanted to the penis is much duller, slower and more insensitive in shrinkage rate than the cancellous tissue of the penis such that the length of the penis pulled towards the front end thereof ("F" direction) markedly prevents the shrinkage of the penis as retained before the operation when the two tissues are sewn together.

After the surgery, the normal length of the penis is consequently maintained with the addition of grafted derma fat (A) in width (G) and the length of the glans, so that circumference of the penis is enlarged as much as the thickness of the derma fat (A) grafted to the skin of (D) the penis.

Furthermore, the derma fat (A) implanted to the penis has the same tissue as the cell tissue of the penis such that the fat (A) is easily assimilated into the tissue of the penis without any side effect.

As many as 150 microcaulia patients who had undergone the surgery according to the present invention have been randomly chosen for survey of obtainment of resultant data in the length and girth of the penis before and after the operation, which is shown in table 1.

TABLE 1

| Time | Patients checked | length (average) | girth (average) |
|---|---|---|---|
| before surgery | 105 | 4.5 Cm | 7.1 Cm |
| 2–3 months after surgery | 82 | 8.3 Cm | 12.1 Cm |
| 4–12 months after surgery | 23 | 8.1 Cm | 11.3 Cm |
| 13–60 months (average 31 months) after surgery | 18 | 8.0 Cm | 10.7 Cm |

Furthermore, degree of satisfaction after the surgery according to the present invention is given in Table 2.

TABLE 2

| 105 Patients checked | greatly improved | a little improved |
|---|---|---|
| Public bath evasive syndrome | 74 (70.5%) | 10 |
| inferiority complex | 77 (73.3%) | 18 |
| sexual self-confidence | 36 (34.3%) | 22 |

Still furthermore, sexual life affected after the surgery according to the present invention is presented in Table 3.

TABLE 3

| 93 patients checked | Improved |
|---|---|
| ejaculation time | 56 (60.2%) |
| partner's satisfaction | 45 (48.4%) |
| patient's satisfaction | 58 (62.4%) |
| erection power | 14 (15.1%) |

As apparent from the foregoing, there is an advantage in the surgically enlarging method of microcaulia in that length and circumference of micropenis are simultaneously enlarged and expanded without incurring any deformation or side effect thereto, thereby enabling the microcaulia neurotics to overcome the physical defect, shame and inferiority complex and providing with increased sexual self confidence.

What is claimed is:

1. A surgically enlarging method of microcaulia, the method comprising the steps of:

tearing off a piece of derma fat from the body of a microcaulia neurotic to put the torn derma fat in cold storage and suturing the vulnus area for cosmetic surgery;

incising the skin of the penis and ablating the same to graft the cold-stored derma fat onto the ablated area of the penis in a state of the penis being maximally pulled to a front area thereof to similarly match the length of the penis; and covering the implanted derma fat with the ablated skin of the penis to suture the covered area and to fix same.

2. The method as defined in claim 1, wherein derma layer is made to face outside of the penis in a bit unfolded state, that is, in a non-stretched state of the derma fat and fat layer is made to face the penis where the widest area of the torn derma fat is positioned at an upper side of the penis and the narrowest area is made to be situated under the penis so that the torn derma fat can be made to be positioned in such a way as to encompass the whole length of the penis including the urethra part such that the torn derma fat (A) should have enough room not to interfere circumferentical expansion of the penis when it is erected.

\* \* \* \* \*